(12) United States Patent
Schmid et al.

(10) Patent No.: US 6,514,730 B1
(45) Date of Patent: Feb. 4, 2003

(54) SECRETION OF HIRUDIN DERIVATIVES

(75) Inventors: Gerhard Schmid, Munich; Paul Habermann, Eppstein, both of (DE)

(73) Assignee: Consortium für elektrochemische Industrie GmbH, München (DE)

( * ) Notice: Subject to any disclaimer, the term of this patent is extended or adjusted under 35 U.S.C. 154(b) by 0 days.

(21) Appl. No.: 09/286,097

(22) Filed: Apr. 2, 1999

Related U.S. Application Data (62) Division of application No. 07/982,064, filed on Nov. 25, 1992, now Pat. No. 5,919,895, which is a continuation of application No. 07/672,791, filed on Mar. 21, 1991, now abandoned.

(51) Int. Cl.$^7$ ............................................. C12P 21/02
(52) U.S. Cl. ........................ 435/69.6; 514/12; 530/324
(58) Field of Search ....................... 530/324; 435/69.1, 435/69.6; 514/12

(56) References Cited

U.S. PATENT DOCUMENTS

| | | | | |
|---|---|---|---|---|
| 4,551,433 A | * | 11/1985 | DeBoer | 435/253 |
| 4,668,662 A | * | 5/1987 | Tripier | 514/2 |
| 5,204,323 A | * | 4/1993 | Findlay et al. | 514/2 |

FOREIGN PATENT DOCUMENTS

| | | | | |
|---|---|---|---|---|
| AU | 4597785 | | 2/1986 | |
| AU | 5233686 | | 7/1986 | |
| AU | 5778786 | | 11/1986 | |
| AU | 7536687 | | 1/1988 | |
| AU | 4365585 | | 11/1989 | |
| DE | 3445517 | | 6/1986 | |
| DE | 3900626 | | 7/1989 | |
| EP | 0025190 | | 3/1981 | |
| EP | 158564 | | 10/1985 | |
| EP | 0168342 | | 1/1986 | |
| EP | 0171024 | | 2/1986 | |
| EP | 0200655 | | 11/1986 | |
| EP | 0225633 | | 6/1987 | |
| EP | 0252854 | | 1/1988 | |
| EP | 0338410 | | 10/1989 | |
| EP | 0352228 | | 1/1990 | |
| EP | 0356335 | | 2/1990 | |
| EP | 0161937 | | 10/1992 | |
| WO | 05143 | * | 5/1990 | 514/12 |

OTHER PUBLICATIONS

J.C. Janson Trends in Biotechnology vol. 2 No. 2, 1984 "Large Scale Affinity Purification–State of the Art and Future Prospects", pp. 31–38.*

FEBS Letters, Bd. 202, Nr. 2, Jun. 1986, p. 373–377; J. Dodt et al.: "Expression, secretion and processing of hirudin in *E. coli* using the alkaline phos–phatase signal sequence".

Applied Microbiology and Biotechnology, Bd. 34, No. 2, Nov. 1990, p. 203–207, Springer–Verlag; E. Bender et al.: "Synthesis and secretion of hirudin by *Streptomyces lividans*".

Biomed. Biochim. Acta 44 (1985) 7/8, 1007–1013 F. Markwardt "Pharmacology of Hirudin: One hundred years after the first report of the anticoagulant agent in medicinal leeches".

FEBS 1104, vol. 165, No. 2, Jan. 1984, Johannes Dodt, Hans–Peter Müller, Ursula Seemüller and Jui–Yoa Chang "The complete amino acid sequence of hirudin, a thrombin specific inhibitor".

Biol. Chem. Hoppe–Seyler, vol. 367, pp. 731–740, Aug. 1968 Cornelia Bermann, Johannes Dodt, Stefanie Köhler, Ernst Fink and Hans Günter Gassen "Chemical Synthesis and Expression of a Gene Coding for Hirudin, the Thrombin–Specific Inhibitor from the Leech".

EP–0225 633, Ciba–Geigy AG, CH–4002 Basel, Plantorgan Werk Heinrich G.E., Christensen KG, (DE), Meyhack et al.

Biol. Chem. Hoppe–Seyler, vol. 366, pp. 379–385, Apr. 1985 Johannes Dodt, Ursula Seemüller, Reinhard Maschler and Hans Fritz "The Complete Covalent Structure of Hirudin".

Communications to the Editor, vol. 83, p. 1510–1511 "Selective Cleavage of the Methionyl Peptide Bonds in Ribonuclease with Cyanogen Bromide".

EP 0 161 937 B1; Nov. 21, 1985; Celltech Ltd., Nagai Kiyoshi et al.

Ann. Rev. Biochem. 1978, 47, 481–532 Joseph M. DiRienzo, Kenzo Nakamura and Masayori Inouye "The outer membrane proteins of gram–negative bacteria: biosynthesis, assembly, and functions".

Journal of Bacteriology, Feb. 1982, p. 434–439, vol. 149, No. 2 Hiroshi Inouye, Wayne Barnes and Jon Beckwith "Signal Sequence of Alkaline Phosphatase of *Escherichia coli*".

(List continued on next page.)

Primary Examiner—James Ketter
(74) Attorney, Agent, or Firm—Collard & Roe, P.C.

(57) ABSTRACT

A process for obtaining hirudin derivatives from *E. coli* secretor mutants which entails:

(1) construction of a recombinant vector on which there is located the gene coding for a hirudin derivative directly downstream of a DNA section which codes for a bacterial signal peptide;

(2) of an *E. coli* secretor mutant with the recombinant vector constructed in step (1);

(3) cultivation of the transformed cells in a medium; and (4) obtaining the hirudin derivative from the medium; and a recombinant vector which contains one or more copies of a gene construct which codes for a protein consisting of a bacterial signal peptide and of a hirudin derivative, and a hirudin derivative with the N-terminal aminoacid sequence A—(SEQ ID NO: 5) in which A represents Ala, Gln, His, Phe, Tyr, Glu, Ser, Asp or Asn.

15 Claims, 5 Drawing Sheets

OTHER PUBLICATIONS

Proc. Natl. Acad. Sci. USA, vol. 77, No. 5, pp. 2621–2625, May 1980, Biochemistry, Joe Hedgpeth, Jean–Marie Clement, Christian Marchal, David Perrin, and Maurice Hofnung "DNA sequence encoding the NH2–terminal peptide involved in transport of λ receptor, an *Escherichia coli* secretory protein".

Nature vol. 285, May 8, 1980, p. 78–81, Huges Bedouelle et al. "Mutations which alter the function of the signal sequence of the maltose binding protein of *Escherichia coli*".

Thrombosis Research 37; 347–350, 1985, Uta Griessbach et al., Institute of Pharmacology and Toxicology Medical Academy Erfurt, G.D.R. "Assay of Hirudin in Plasma using a chromogenic thrombin substrate".

"Hirudin: A Family of Iso–Proteins Isolation and Sequence Determination of New Hirudins," ISSN 0323–4347, *Folia Haematol*, Leipzig 115 (1988) 1–2, S. 30–35.

"Primary Structures of New 'Iso–hirudins'," *FEBS Letters*, vol. 225, No. 1, p. 105–110 (1989).

* cited by examiner

Fig. 2: DNA-SEQUENCE OF THE SYNTHETIC HIRUDIN GENE FROM pK152

```
                    Hinf I
         20          40              60
          .           .       .       .
acgtatactgactgcactgaatctggtcagaacctgtgcctgtgcgaaggatctaacgtt
tgcatatgactgacgtgacttagaccagtcttggacacggacacgcttcctagattgcaa ThrTyrThrAspCysThrGluSerGlyGlnAsnLeuCysLeuCysGluGlySerAsnVal Bam HI
         80              100             120
          .       .       .       .       .
tgcggccagggtaacaaatgcatccttggatccgacggtgaaaagaaccagtgcgttact
acgccggtcccattgtttacgtaggaacctaggctgccacttttcttggtcacgcaatga CysGlyGlnGlyAsnLysCysIleLeuGlySerAspGlyGluLysAsnGlnCysValThr 140             160             180
          .       .       .       .       .       .
ggcgaaggtaccccgaaaccgcagtctcataacgacggcgacttcgaagagatccctgag
ccgcttccatggggctttggcgtcagagtattgctgccgctgaagcttctctagggactc GlyGluGlyThrProLysProGlnSerHisAsnAspGlyAspPheGluGluIleProGlu 200             220     Hind III
          .       .       .       .       .
gaataccttcagtaatagagctcgtcgacctgcaggcatgcaagctt
cttatggaagtcattatctcgagcagctggacgtccgtacgttcgaa GluTyrLeuGlnEndEnd
```

Fig. 3: DNA-SEQUENCE OF OLIGONUCLEOTIDES

HIR 1:

```
Pst I                              Hinf I
      acgtatactgactgcactg
acgttgcatatgactgacgtgactta
  Ala Thr Tyr Thr Asp Cys Thr Glu
```

HIR 2:

```
Pst I                                            Hinf I
      acgcgtcttacgtatactgactgcactg
acgttgcgcagaatgcatatgactgacgtgactta
  Ala Thr Arg Leu Thr Tyr Thr Asp Cys Thr Glu
```

HIR 3:

```
Sph I                                                            Hinf I
      cagacgattgctcttacgtatactgactgcactg
gtacgtctgctaacgagaatgcatatgactgacgtgactta
  Glu Thr Ile Ala ↑ Leu Thr Tyr Thr Asp Cys Thr Glu
```

SIGNAL PEPTIDE ──── α-CGTase

SECRETION OF HIRUDIN DERIVATIVES

CROSS-REFERENCE TO RELATED APPLICATIONS

This patent application is a divisional patent application of U.S. patent application Ser. No. 07/982,064 filed Nov. 25, 1992, now U.S. Pat. No. 5,919,895, which is a continuation patent application of U.S. patent application Ser. No. 07/672,791 filed Mar. 21, 1991, now abandoned.

BACKGROUND OF THE INVENTION

1. Field of the Invention

The present invention relates to a process for obtaining hirudin derivatives from *E. coli* secretor mutants, and to a hirudin derivative with the N-terminal amino-acid sequence (SEQ ID NO: 1).

2. The Prior Art

Hirudin is a polypeptide with 65 amino acids and was originally isolated from the leach *Hirudo medicinalis*. It acts as a highly specific inhibitor of thrombin by forming stable complexes with thrombin and, therefore, has many possible therapeutic uses, especially for anticoagulation therapy (F. Markquardt, Biomed. Biochim. Acta 44 (1985), 1007–1013).

The publication of the complete amino-acid sequence of hirudin (J. Dodt et al., FEBS LETTERS 165 (2), (1984), 180–184) was the prerequisite for the preparation of hirudin by recombinant DNA techniques and expression in microorganisms.

European Patent Application No. 158,564 (Transgene) discloses cloning vectors for the expression of hirudin or hirudin analogues in a host cell, especially a bacterial cell. The gene coding for hirudin is, in this case, obtained by cDNA synthesis starting from mRNA from the leach *Hirudo medicinalis*. Described, in particular, is a hirudin derivative with the N-terminal sequence (SEQ ID NO: 2) and processes for obtaining it.

European Patent Application No. 168,342 (Ciba Geigy) discloses DNA sequences which code for the natural amino-acid sequence of hirudin, wherein the N-terminal amino-acid sequence is (SEQ ID NO: 3). The expression of hirudin takes place intracellularly in the microorganisms *E. coli* and *Saccharomyces cerevisiae*.

European Patent Application No. 171,024 (Hoechst AG) discloses a process for the genetic engineering for preparation of polypeptides with hirudin activity, in particular, in *E. coli* cells, wherein the cells are disrupted and the polypeptide with hirudin activity is obtained from the cell extract. A fusion protein portion which is present where appropriate can be deleted by proteolytic or chemical cleavage, and the liberated hirudin molecule can be purified.

German Patent Application No. 3,445,571 (GEN-BIO-TEC) relates to a DNA sequence which codes for a protein with the biological activity of hirudin, and to a process for obtaining such proteins from *E. coli* cells which are transformed with a suitable recombinant vector by lysis of the cells.

The paper by Bergmann et al (Biol. Chem. Hoppe Seyler 367 (1986), 731–740) also describes hirudin synthesis in *E. coli*. The hirudin is released from the cells by toluene treatment, with only low yields of about 500 ng/l $A_{578}$ units of cells being achieved.

European Patent Application No. 200,655 (Transgene), European Patent Application No. 252,854 (Transgene), and European Patent Application No. 225,633 (Ciba Geigy) disclose the obtaining by secretion of proteins with hirudin activity from a eukaryotic host organism, especially yeast, wherein the expression takes place on a vector which contains a DNA sequence which contains a signal peptide upstream of the structural gene. The secretion of hirudin derivatives with the N-terminal sequence (SEQ ID NO: 3) and with the N-terminal sequence (SEQ ID NO: 2) in yeast is disclosed. In this case, yields of up to 100 mg/l are reported.

German Patent Application No. 3,900,626 (Hoechst AG) discloses a hirudin derivative with the N-terminal sequence (SEQ ID NO: 4). The expression takes place preferably in yeast, using the promoter and signal sequence of the yeast pheromone gene MFα for the expression and secretion of the hirudin derivative.

All the processes described above for preparing hirudin derivatives have disadvantages, however. Thus, when yeast is used as the host organism, and the hirudin is secreted into the culture medium, relatively high yields are obtained, but the cultivation of yeast cells takes longer and is more demanding than that of bacteria, for example, *E. coli*. However, on the other hand, in *E. coli* cells, the yield is relatively low, and/or complicated isolation processes are necessary on disruption of the cells.

SUMMARY OF THE INVENTION

Accordingly, it is an object of the present invention to develop a straightforward process for obtaining hirudin derivatives in which hirudin derivatives can be obtained in high yield from bacterial cells without entailing the necessity of disruption of the cells.

The present invention relates to a process for obtaining hirudin derivatives from *E. coli* secretor mutants which entails:

(1) construction of a recombinant vector on which there Is located the gene coding for a hirudin derivative downstream of a DNA section which codes for a bacterial signal peptide;

(2) transforming an *E. coli* secretor mutant with the recombinant vector constructed in step (1);

(3) cultivating the transformed cells in a medium; and (4) obtaining the hirudin derivative from the medium.

The term "hirudin derivative," according to the present invention, refers to proteins which are derived from hirudin which act as thrombin inhibitors and have a specific activity of at least 10,000 AT-U/mg (antithrombin units) (Dodt et al., Biol. Chem. Hoppe Seyler 366 (1985), 379–385). The term "hirudin derivative" also comprises fusion proteins with an N-terminal fusion portion which is up to about 50 amino acids long and can be partially or completely deleted by proteolytic or chemical cleavage, resulting in, as a cleavage product, a hirudin derivative of a specific activity of at least 10,000 AT-U/mg.

Preferably obtained by the process according to the invention are hirudin derivatives with the following N-terminal amino-acid sequence:

$(X)_m$—Z—                                                       (SEQ ID NO: 5)

in which

| | |
|---|---|
| m | 0 to 50; |
| x | represents identical or different genetically encodable amino acids; |
| z | represents a genetically encodable amino acid from the group comprising Leu, Ile, Ala, Val, Gly, Ser, Asp, Glu, Asn, Gln, His, Met, Phe and Tyr. |

Where m is greater than 0, the sequence X preferably contains a proteolytic or chemical cleavage site, particularly preferably at its end. If, for example, the last amino acid in the sequence X is an Arg residue, the fusion sequence X can be cleaved off by digestion-with trypsin (cleavage after Arg), and the active hirudin derivative can be purified. However, it is equally possible to cleave off the fusion portion using other known proteolytic enzymes or chemical cleavage reagents. If, for example, the amino-acid sequence of X terminates with a Met residue, the fusion protein can be cleaved by cleavage with cyanogen halides (E. Gross and B. Wittkop, J. Am. Chem. Soc. 82 (1961) 1510–1517). If, for example, the C-terminal amino-acid sequence of X contains the amino-acid sequence (SEQ ID NO: 6), the cleavage can be carried out with factor Xa (European Patent Application No. 25,190 and European Patent Application No. 161,973).

When m=0, in the process according to the invention, Z preferably represents Ala, Gln, His, Phe, Tyr, Gly, Ser, Asp or Asn, particularly preferably Ala, Gly, Ser, Asp or Asn. Maximum preference is given to a hirudin derivative in which m denotes 0 and Z represents Ala.

Thus, the present invention also relates to hirudin derivatives with the N-terminal sequence A—(SEQ ID NO: 5) in which A represents Ala, Gln, His, Phe, Tyr, Gly, Ser, Asp or Asn, preferably Ala, Gly, Ser, Asp or Asn. Maximum preference is given to a derivative with the N-terminal sequence (SEQ ID NO: 1). Surprisingly, it has been possible to obtain from this hirudin derivative in the culture supernatant of an E. coli secretor mutant up to above 2 g/l medium of active hirudin.

Another advantage of the process according to the invention is that, owing to the secretion of the hirudin derivative into the cell medium, the disulfide linkages of hirudin are correctly formed under the oxidative conditions of the medium.

According to the present invention, the term E. coli secretor mutants is intended to refer to E. coli strains which show massive protein secretion into the culture medium. A process for preparing these secretor mutants is disclosed in European Patent No. 338,410. The obtaining of suitable E. coli secretor mutants can start from, in particular, E. coli DS410 (DSM 4513) or E. coli BW7261 (DSM 5231). The particular E. coli strain is initially transformed with a plasmid which contains a DNA sequence coding for a secretable protein. The transformed E. coli strain is then subjected to a mutagenesis, for example, by treatment with N-methyl-N'-nitro-N-nitrosoguanidine. This is followed by selection for suitable secretor mutant strains. If the secretable protein used is, for example, α-cyclodextrin glycosyltransferase, secretor mutants can be recognized by resistance to the substance D-cycloserine, which is active on the cell wall. In addition, the secretion of α-cyclodextrin glycosyltransferase (CGTase) brings about hydrolysis of the starch in the surrounding medium, which provides an additional option for selection of secretor mutants when an amylopectin azure medium is used.

Suitable as recombinant vectors for the present invention are vectors which either are able to integrate into the E. coli genome (for example, bacteriophageλ) or are present extra-chromosomally in the transformed E. coli cell (for example, plasmids). Plasmids are preferably used.

The gene construct which is on the recombinant vector and which codes for a protein consisting of signal peptide and the hirudin derivative is preferably under the control of an inducible promoter, particularly preferably of a trp-lac fusion promoter which is inducible by addition of lactose or IPTG (isopropylβ-D-thiogalactoside). In addition, a selection marker gene and, where appropriate, a lac repressor gene, should be present on the vector.

Suitable as a bacterial signal sequence which makes secretion of the hirudin derivative possible are, in principle, all known signal peptides which allow a permeation of the membrane of E. coli cells. Thus, also preferably used are signal peptides from Gram-negative bacteria as (for example, signal peptides of the following proteins of E. coli: outer membrane protein OmpA (DiRienzo et al, Ann. Rev. Biochem. 47 (1978) 481–532); alkaline phosphatase PhoA (Inouye et al, J. Bacteriol. 149 (1982) 434–439); LamB protein (Hedgpeth et al, Proc. Nat. Acad. Sci. USA 77 (1980) 2621–2625); Maltose binding protein MalE (Bedouelle et al, Nature 285 (1980) 78–81). The α-CGTase signal peptide is particularly preferably used.

Figure 1:
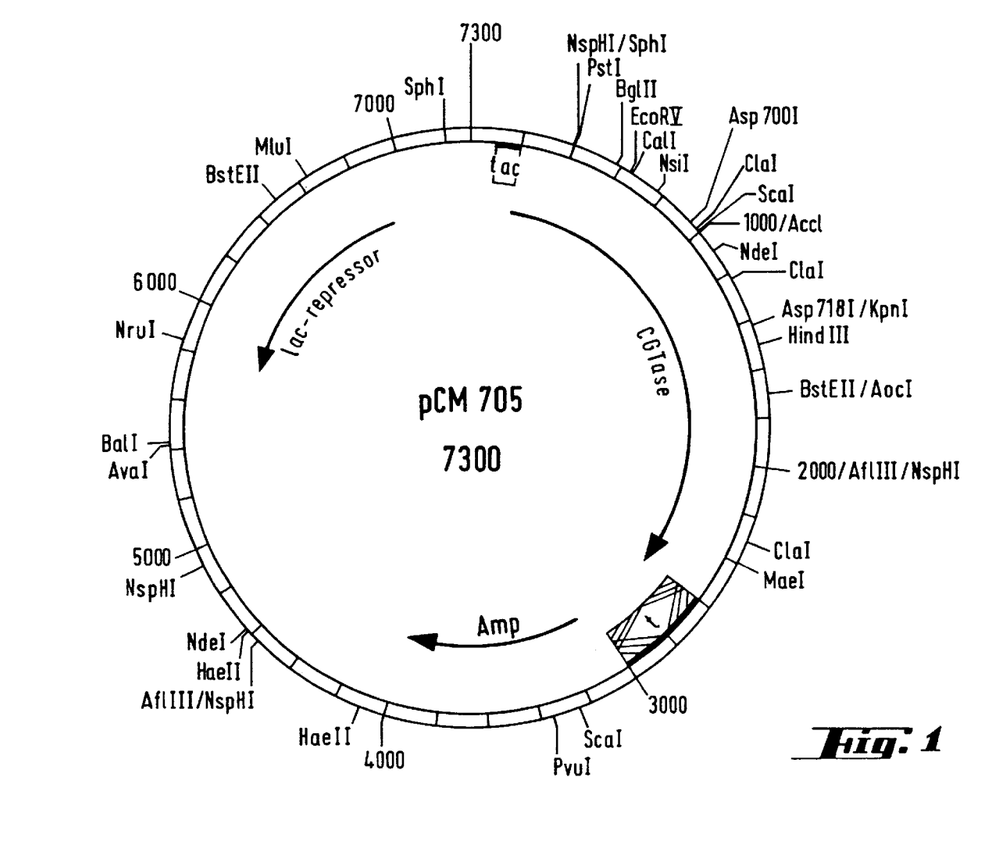
FIG. 1 shows the plasmid pCM705.

An example of a vector suitable for the process according to the invention is the plasmid pCM705 (FIG. 1), which can be obtained from the plasmid pCM703 disclosed in European Patent Application No. 383,410, by deletion of an NruI fragment which is about 1 kb long. This vector contains an ampicillin-resistance gene, the gene for the lac repressor and the CGTase gene with a section coding for the signal peptide at the 5' end. A gene coding for a hirudin derivate is integrated into the vector pCM705 in such a way that there is intracellular production of a precursor molecule with the signal peptide of the α-CGTase at its N-terminal end. The gene construct is under the control of the tac promoter. An E. coli secretor mutant strain can be transformed with the plasmid obtained in this way.

Positively transformed clones are cultivated in a shaken flask or in a fermenter. Induction by IPTG (isopropyl-β-D-thiogalactoside) or lactose is carried out when an optical density ($OD_{600}$) of about 1 is reached.

The progress of the production of the hirudin derivative is then determined by means of a thrombin inactivation test (Griesbach et al, Thrombosis Research 37, (1985), 347–350). The accumulation of fusion proteins is analyzed by HPLC chromatography (reversed phase). The proportion of fusion proteins can then be cleaved off, and the resultant active hirudin derivative can be purified.

BRIEF DESCRIPTION OF THE DRAWINGS

Other objects and features of the present invention will become apparent from the following detailed description considered in connection with the accompanying drawings which discloses a few embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Example 1

Construction of the Secretion Vector

Figure 2:
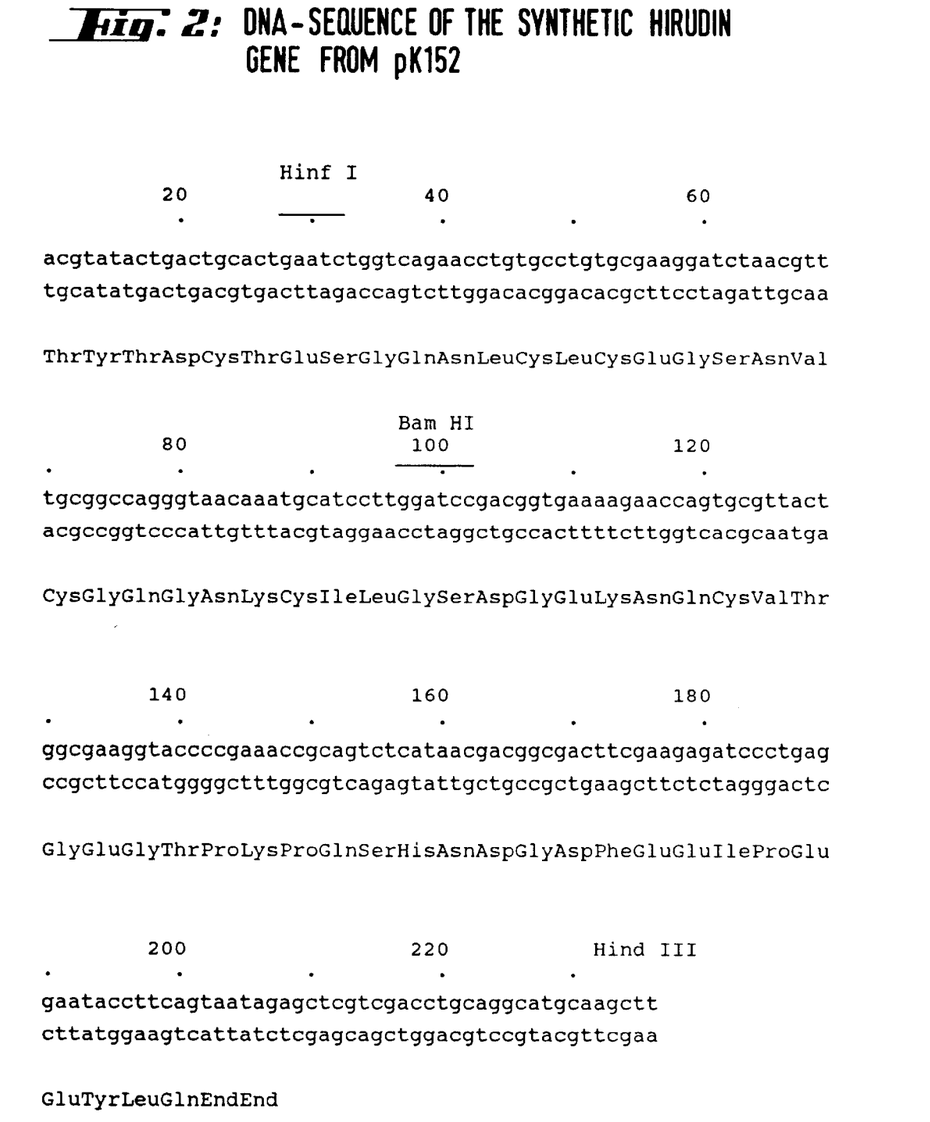
FIG. 2 shows the DNA sequence of the synthetic hirudin gene from pK152.
Figure 3:
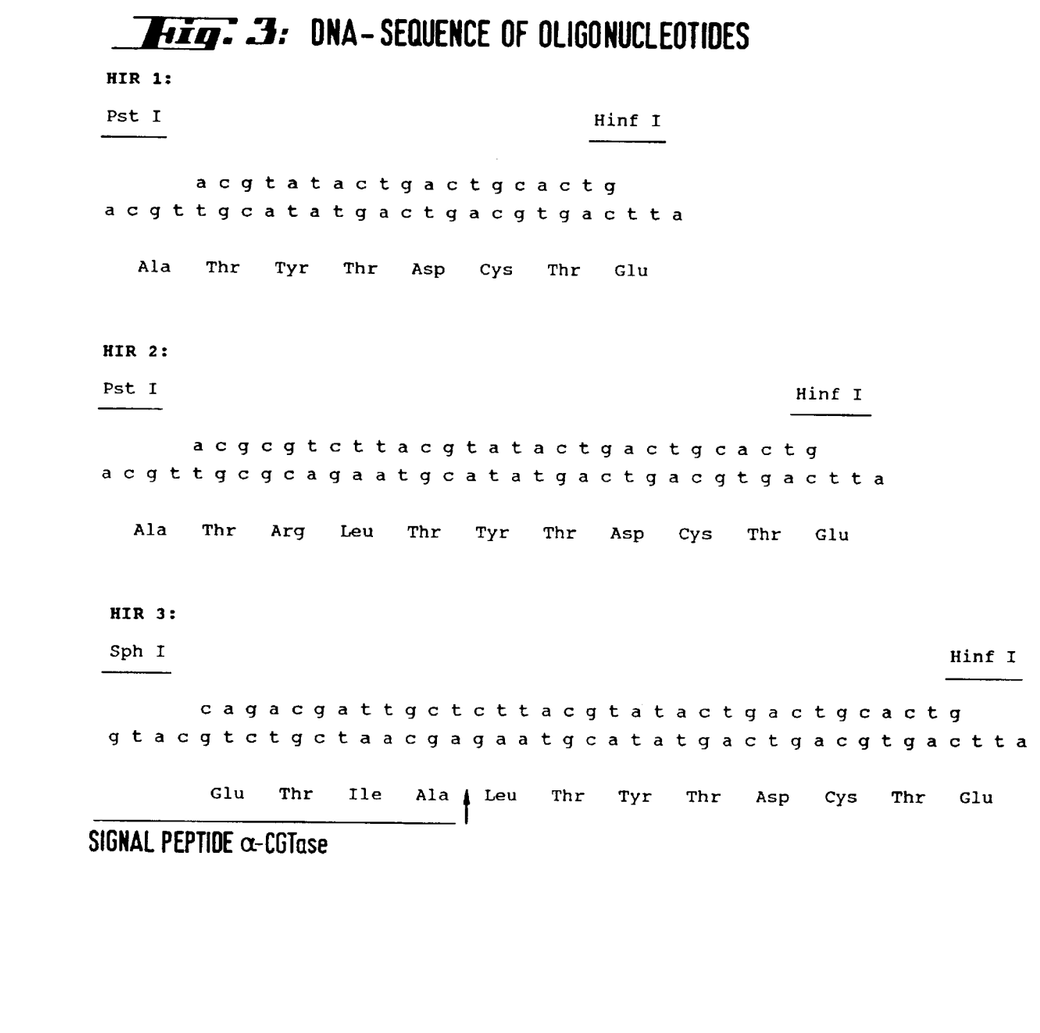
FIG. 3 shows the sequences of the oligonucleotide HIR1, HIR2 and HIR3.

The plasmid pK152 harbors a synthetic hirudin gene whose sequence is listed in European Patent Application No. 171,024. Starting from this plasmid, a HinfI-HindIII DNA fragment which is about 200 bp in size and which comprises most of the DNA sequence which codes for hirudin was isolated by agarose gel electrophoresis (FIG. 2). The missing 5'-terminal sequence is regenerated by a newly synthesized oligonucleotide (HIR 1). The coding sequence of the oligonucleotide is shown in FIG. 3. Fusion of the HinfI ends results in a hirudin derivative with the N-terminal sequence (SEQ ID NO: 1).

The plasmid pCM705 (FIG. 1) is cleaved with PstI and HindIII. The two cleavage sites are located in the coding region for the gene CGTase, which results in a DNA fragment about 1 kb in size being cut out. PstI cleaves exactly in the region which codes for the signal peptidase cleavage site.

Figure 4:
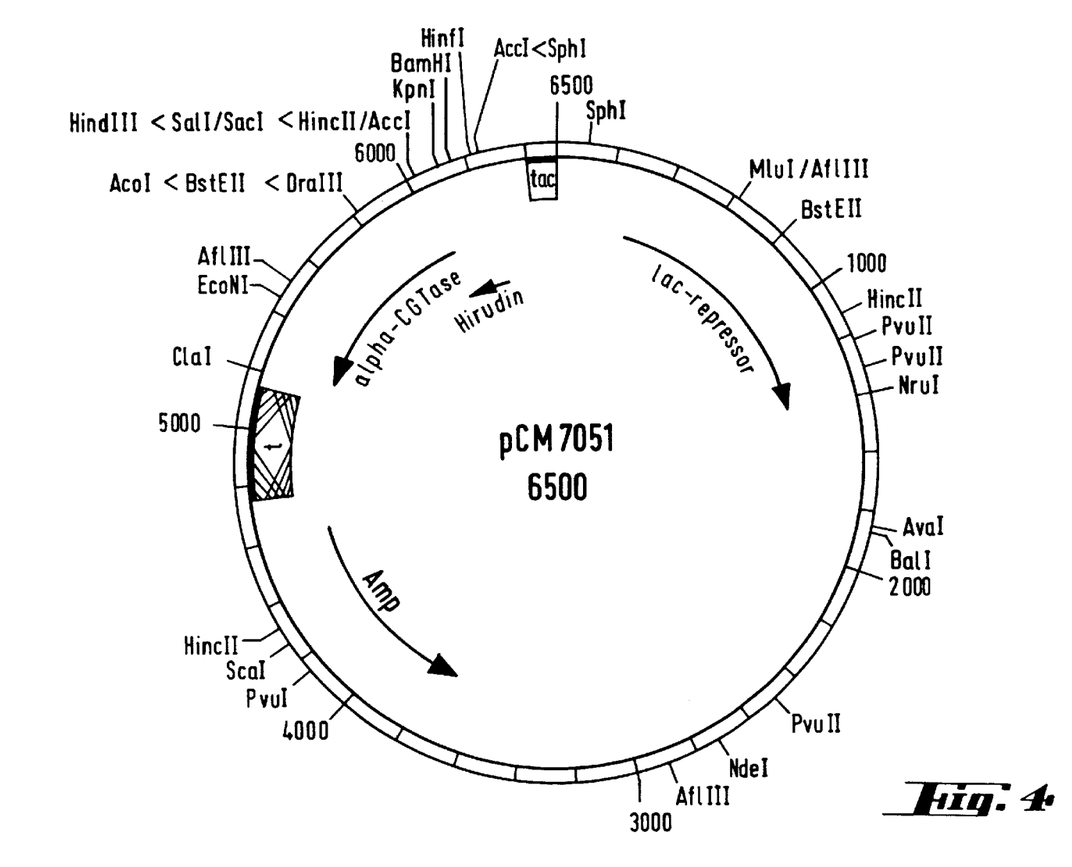
FIG. 4 shows the plasmid pCM7051.

The fragments pCM705 PstI-HindIII 6.3 kb, pK152 HinfI-HindIII 0.2 kb and the oligonucleotide HIR 1 are ligated together, which results in the plasmid pCM7051 (FIG. 4). The ligation mixture is used to transform the E. coli HB101 (DSM 1607). Colonies which show no zones of starch breakdown on selective medium containing amylopectin azure (colored amylopectin) and thus show no α-CGTase expression are isolated and purified to homogeneity. Plasmid DNA is isolated from several purified clones and is characterized by restriction analysis. Two plasmids which have a hirudin insert are subjected to sequence analysis of the fusion regions.

Plasmid DNA which has a correct hirudin gene construction is cleaved with NruI and NdeI, and a fragment 5.18 kb in size is isolated by agarose gel electrophoresis.

Figure 5:
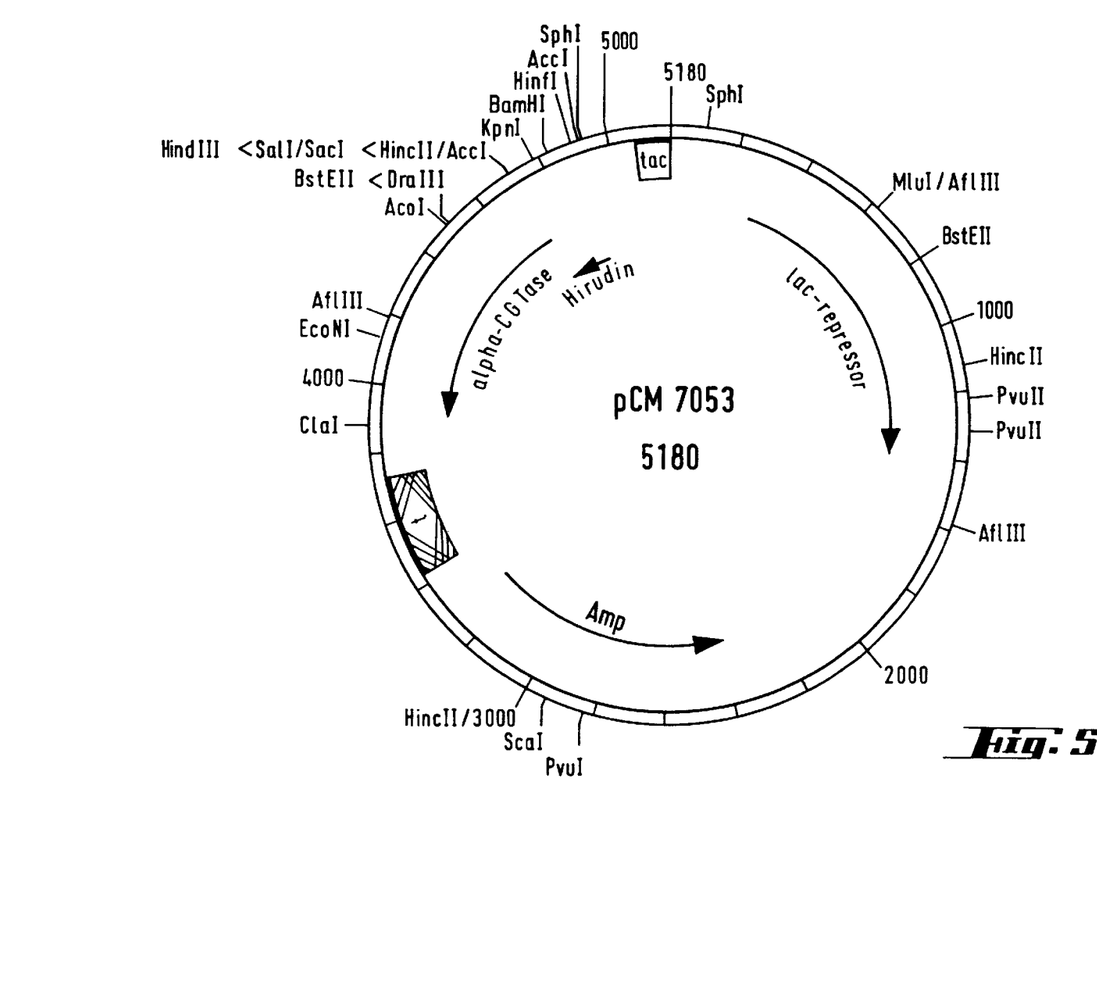
FIG. 5 shows the plasmid pCM7053.

After the sequence which protrudes owing to NdeI cleavage has been filled in with Klenow enzyme, the fragment is circularized by ligation. The resulting plasmid is called pCM7053 (FIG. 5).

This plasmid pCM7053 is used to transform the secretor mutant E. coli WCM100 which was obtained by the method described in European Patent Application No. 338,410.

Example 2

Test for Secretion of Hirudin in Shake Flask Experiments 10 ml of LB medium containing 100 μg/ml ampicillin were inoculated with a fresh overnight culture of WCM100 pCM7053 to the optical density $OD_{420}$=0.1. The culture is shaken at 30° C. As soon as the optical density $OD_{420}$=1.0 is reached, the inducer lactose is added to a final concentration of 1%. After 48 hours, examples of the culture are taken, the cells are spun down, and the hirudin concentration in the supernatant is determined. The determination is carried out by a thrombin inactivation test. Yields of up to 4000 AT-U/ml (antithrombin units) were determined (≙250 mg/l).

Example 3

Hirudin Production in a 10 l Fermenter 7 l of minimal medium containing 100 μg/ml ampicillin are inoculated with a fresh overnight culture of WCM100 pCM7053 to the optical density $OD_{600}$=0.1. The fermentation conditions are:

Temperature: 30° C.

Stirring Rate: 450 to 950 rpm

Aeration: 0.5 to 1.5 Vvm pH: 7.0±0.1

When the optical density $OD_{600}$=1.0 is reached, 0.5 mM IPTG (isopropylβ-D-thiogalactoside) is added.

40 hours after addition of IPTG, it was possible to determine 36,000 AT-U/ml in the supernatant (≙2.25 g/l).

Example 4

Secretion of Hirudin with the N-Terminal Sequence (SEQ ID NO: 7)

When a procedure analogous to Example 1 is carried out, but the oligonucleotide HIR 2 (FIG. 3) is used in place of the oligonucleotide HIR 1, the result is a hirudin fusion protein after cleavage off of the signal peptide with the N-terminal sequence (SEQ ID NO: 7). The accumulation of this fusion protein in the supernatant is determined by HPLC analysis using reversed phase conditions ($C_{18}$ chromatography column). The fermentation of the strain WCM100 with this gene construct produced a yield of 25 mg/l fusion protein.

Active hirudin with the N-terminal sequence (SEQ ID NO: 4) can be achieved by trypsin cleavage.

Example 5

Secretion of Hirudin with the Secretor Mutant WCM88

The secretor mutant WCM88, which was likewise obtained in the manner described in European Patent Application No. 338,410, is transformed with the plasmid pCM7053 (see Example 1). The production of hirudin by secretion into the culture medium is tested in shake flask experiments and fermentations.

(a) Shake Flask Experiments—The strain WCM88 pCM7053 is cultivated analogously to Example 2. The hirudin concentration in the supernatant of the culture is determined after 48 hours. Yields of up to 1800 AT-U/ml were achieved (≙110 mg/l).

(b) Production in a 10 l Fermenter—The strain was cultivated as described in Example 3. 45 hours after addition of IPTG, it was possible to detect 21,000 AT-U/ml in the supernatant (≙1.3 g/l).

Example 6

Construction of a Secretion Vector Carrying a Tetracyclin Resistance Gene

A 1.1 kb NruI-fragment of the plasmid pBR322 [F. Bolivar et al. Gene 2, 95–113 (1977)] was isolated and ligated with a linearized form of pCM7051 which was cleaved by NruI. The ligation mixture was used to transform E. coli HB101. Transformants were selected for tetracyclin resistance. Plasmid-DNA was re-isolated from a selected clone and cleaved by NdeI and AvaI. After isolation of the larger fragment by agarose gel electrophoresis, the sticky ends were filled in by Klenow enzyme and then ligated.

The resulting plasmid was pCMT203.

Example 7

Secretion of Hirudin Using the Secretion Vector PCMT203

The secretion mutant WCM100 was transformed with plasmid pCMT203. This strain was cultivated in a 10 l fermenter, as described in Example 3. After 45 h of addition of IPTG, the yields were 42,000 AT-U/ml of hirudin.

The DNA sequence of the synthetic hirudin gene from pK152, as shown in FIG. 2, is set forth in (SEQ ID NO: 8).

The DNA sequence of oligonucleotides, as shown in FIG. 3, is set forth in (SEQ ID NO: 9), (SEQ ID NO: 10), (SEQ ID NO: 11), (SEQ ID NO: 12), (SEQ ID NO: 13) and (SEQ ID NO: 14).

While only a few embodiments of the present invention have been shown and described, it is to be understood that many changes and modifications may be made thereunto without departing from the spirit and scope of the invention as defined in the appended claims.

What is claimed is:

1. Process for obtaining hirudin derivatives from *E. coli* secretor mutants comprising the steps:

(1) constructing a recombinant vector on which there is located the gene coding for a hirudin derivative directly downstream of a DNA section which codes for a bacterial signal peptide;
wherein the signal peptide originates from α-cyclodextrin glycosyltransferase gene;

(2) transforming *E. coli* secretor mutant cells using the recombinant vector constructed in step (1);

(3) cultivating the transformed cells of step (2) in a medium; and (4) obtaining the hirudin derivative from the medium.

2. Process according to claim 1, wherein a plasmid is used as said recombinant vector.

3. Process according to claim 1, comprising constructing a recombinant vector on which the DNA sequences coding for the hirudin derivative and for the signal peptide are located under the control of an inducible promoter.

4. Process according to claim 3, comprising using a trp-lac fusion promoter as said inducible promoter.

5. Process according to claim 1, comprising using a signal peptide from Gram-negative bacteria.

6. Process according to claim 1, wherein a bacterial strain which has been obtained by mutagenesis and subsequent selection for secretion properties from the *E. coli* strains DS410 or BW 7261 is used as *E. coli* secretor mutant.

7. Recombinant vector comprising one or more copies of a gene construct which codes for a protein comprising a bacterial signal peptide and a hirudin derivative; and
wherein the signal peptide originates from α-cyclodextrin glycosyltransferase gene.

8. Process for obtaining hirudin derivatives from *E. coli* secretor mutants comprising the steps:

(1) constructing a recombinant vector on which there is located the gene coding for a hirudin derivative directly downstream of a DNA section which codes for a bacterial signal peptide;

(2) transforming *E. coli* secretor mutant cells using the recombinant vector constructed in step (1);

(3) cultivating the transformed cells of step (2) in a medium; and (4) obtaining the hirudin derivative from the medium, wherein said hirudin derivative has the following N-terminal amino-acid sequence:

$(X)_m$—Z—           (SEQ ID NO: 5)

in which
m=0 to 50;
X represents identical or different genetically encodable amino acids; and
Z represents a genetically encodable amino acid selected from the group consisting of His, Leu, Ile, Ala, Val, Gly, Ser, Asp, Glu, Asn, Gln, Met, Phe and Tyr.

9. Process according to claim 8, wherein the sequence X contains a proteolytic or chemical cleavage site.

10. Process according to claim 8, wherein m=0 and Z is Ala, Gln, His, Phe, Tyr, Gly, Ser, Asp or Asn.

11. Process according to claim 10, wherein Z is Ala, Gly, Ser, Asp or Asn.

12. Process according to claim 11, wherein Z is Ala.

13. Recombinant DNA comprising DNA which codes for a hirudin derivative and
said hirudin derivative contains an N-terminal sequence A—(SEQ ID NO: 5) in which A is selected from the group consisting of Ala, Gln, His, Phe, Tyr, Gly, Ser, Asp and Asn.

14. Recombinant vector comprising one or more copies of a gene construct which codes for a protein comprising a bacterial signal peptide and a hirudin derivative; and wherein the hirudin derivative has the following N-terminal amino-acid sequence:

(X)$_m$—Z— (SEQ ID NO: 5)

in which
m=0–50;
X represents identical or different genetically encodable amino acids; and
Z represents a genetically encodable amino acid selected from the group consisting of His, Leu, Ile, Ala, Val, Gly, Ser, Asp, Glu, Asn, Gln, Met, Phe and Tyr.

15. Recombinant vector according to claim 14, wherein the hirudin derivative has the N-terminal sequence (SEQ ID NO: 1).

* * * * *

UNITED STATES PATENT AND TRADEMARK OFFICE
CERTIFICATE OF CORRECTION

PATENT NO. : 6,514,730 B1
DATED : February 4, 2003
INVENTOR(S) : Gerhard Schmid and Paul Habermann It is certified that error appears in the above-identified patent and that said Letters Patent is hereby corrected as shown below:

<u>Title page,</u>
Item [30], Foreign Application Priority Data correctly should read:

-- March 22, 1990    (DE) ………………….. 40 09 268 --.

Signed and Sealed this

Fifth Day of August, 2003

JAMES E. ROGAN
*Director of the United States Patent and Trademark Office*

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 1

Ala Thr Tyr Thr Asp
1               5

<210> SEQ ID NO 2
<211> LENGTH: 5
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 2

Ile Thr Tyr Thr Asp
1               5

<210> SEQ ID NO 3
<211> LENGTH: 5
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 3

Val Val Tyr Thr Asp
1               5

<210> SEQ ID NO 4
<211> LENGTH: 5
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein
```

```
<400> SEQUENCE: 4

Leu Thr Tyr Thr Asp
1               5

<210> SEQ ID NO 5
<211> LENGTH: 4
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 5

Thr Tyr Thr Asp
1

<210> SEQ ID NO 6
<211> LENGTH: 4
<212> TYPE: PRT
<213> ORGANISM: Artificial Sequence
<220> FEATURE:
<221> NAME/KEY: misc_feature
<223> OTHER INFORMATION: Description of Artificial Sequence:  Human
      amino acids

<400> SEQUENCE: 6

Ile Glu Gly Arg
1

<210> SEQ ID NO 7
<211> LENGTH: 8
<212> TYPE: PRT
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 7

Ala Thr Arg Leu Thr Tyr Thr Asp
1               5

<210> SEQ ID NO 8
<211> LENGTH: 227
<212> TYPE: DNA
<213> ORGANISM: Artificial Sequence
<220> FEATURE:
<221> NAME/KEY: CDS
<222> LOCATION: (1)..(192)
<223> OTHER INFORMATION: Description of Artificial Sequence:  Hirudin
      protein

<400> SEQUENCE: 8 acg tat act gac tgc act gaa tct ggt cag aac ctg tgc ctg tgc gaa      48
Thr Tyr Thr Asp Cys Thr Glu Ser Gly Gln Asn Leu Cys Leu Cys Glu
1               5                   10                  15 gga tct aac gtt tgc ggc cag ggt aac aaa tgc atc ctt gga tcc gac      96
Gly Ser Asn Val Cys Gly Gln Gly Asn Lys Cys Ile Leu Gly Ser Asp
            20                  25                  30 ggt gaa aag aac cag tgc gtt act ggc gaa ggt acc ccg aaa ccg cag     144
Gly Glu Lys Asn Gln Cys Val Thr Gly Glu Gly Thr Pro Lys Pro Gln
        35                  40                  45 tct cat aac gac ggc gac ttc gaa gag atc cct gag gaa tac ctt cag     192
Ser His Asn Asp Gly Asp Phe Glu Glu Ile Pro Glu Glu Tyr Leu Gln
    50                  55                  60
```

-continued taatagagct cgtcgacctg caggcatgca agctt                                                                            227

<210> SEQ ID NO 9
<211> LENGTH: 64
<212> TYPE: PRT
<213> ORGANISM: Artificial Sequence
<220> FEATURE:
<223> OTHER INFORMATION: Description of Artificial Sequence:  Hirudin
      protein

<400> SEQUENCE: 9

Thr Tyr Thr Asp Cys Thr Glu Ser Gly Gln Asn Leu Cys Leu Cys Glu
1               5                   10                  15

Gly Ser Asn Val Cys Gly Gln Gly Asn Lys Cys Ile Leu Gly Ser Asp
            20                  25                  30

Gly Glu Lys Asn Gln Cys Val Thr Gly Glu Gly Thr Pro Lys Pro Gln
        35                  40                  45

Ser His Asn Asp Gly Asp Phe Glu Glu Ile Pro Glu Glu Tyr Leu Gln
    50                  55                  60

<210> SEQ ID NO 10
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 10
acgtatactg actgcactg                                                                                              19

<210> SEQ ID NO 11
<211> LENGTH: 26
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 11
acgttgcata tgactgacgt gactta                                                                                      26

<210> SEQ ID NO 12
<211> LENGTH: 28
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 12
acgcgtctta cgtatactga ctgcactg                                                                                    28

<210> SEQ ID NO 13
<211> LENGTH: 35
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein -continued

```
<400> SEQUENCE: 13
acgttgcgca gaatgcatat gactgacgtg actta                              35

<210> SEQ ID NO 14
<211> LENGTH: 34
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 14
cagacgattg ctcttacgta tactgactgc actg                               34

<210> SEQ ID NO 15
<211> LENGTH: 41
<212> TYPE: DNA
<213> ORGANISM: Artificial Sequence
<220> FEATURE:
<221> NAME/KEY: misc_feature
<223> OTHER INFORMATION: Description of Artificial Sequence:  Hirudin
      protein

<400> SEQUENCE: 15
gtacgtctgc taacgagaat gcatatgact gacgtgactt a                       41
```